United States Patent [19]

Antonio Barrio Calle et al.

[11] Patent Number: 5,321,175
[45] Date of Patent: Jun. 14, 1994

[54] OLEFIN HYDROGENATION PROCEDURE

[75] Inventors: Juan Antonio Barrio Calle; Maria Dolores Parellada Ferrer, both of Madrid; Agreda Tomas C., Guadalajara; Juan C. F. Serrano; Pascual R. Gracia, both of Madrid, all of Spain

[73] Assignee: Repsol Quimica S.A., Spain

[21] Appl. No.: 986,462

[22] Filed: Dec. 4, 1992

[30] Foreign Application Priority Data

Dec. 5, 1991 [ES] Spain .................................. 9102732

[51] Int. Cl.$^5$ ................................................ C07C 2/74
[52] U.S. Cl. ..................................... 585/255; 585/250; 585/267; 585/275; 585/400; 585/418; 585/700
[58] Field of Search ............... 585/250, 255, 267, 275, 585/400, 418, 700

[56] References Cited

U.S. PATENT DOCUMENTS 3,784,481  1/1974  Lassau et al. ........................ 585/250

Primary Examiner—Patrick P. Garvin
Assistant Examiner—E. D. Irzinski
Attorney, Agent, or Firm—Kolisch, Hartwell, Dickinson, McCormack & Heuser

[57] ABSTRACT

Procedure of olefin hydrogenation in liquid phase in the presence of homogeneous catalysts that contain, as essential component, a titanocene of general formula $Cp^{\ast}CpTiR_2$, $Cp \wedge CpTiR_2$, $Cp \wedge Cp[CpTiR_2]_2$, or $Cp \wedge Cp[Cp^{\ast}TiR_2]_2$ where $Cp^{\ast}$ is a pentamethylcyclopentadienyl, Cp cyclopentadienyl, $Cp \wedge Cp$ are two cyclopentadienyl rings linked together by a dimethylsililene ($Me_2Si$), and R is an alyl, aryl, alkylaryl, or alcoxide group containing between 1 and 20 carbon atoms or a halogen atom, a $PPh_2$, $CH_2SiMe_3$, $CH_2PPh_2$, or H.

These catalysts are very active in the hydrogenation of linear and branched, internal and external olefins, cyclo-olefins and diolefins. In addition, they are able to selectively hydrogenate double bonds of diene groups in conjugated diene polymers and copolymers, of medium molecular weight between approximately 500 and 1,000,000 and, in particular the random copolymers and styrene and butadiene or isoprene block copolymers, containing the latter at least one styrene block and a polybutadiene and/or isoprene block.

10 Claims, No Drawings

OLEFIN HYDROGENATION PROCEDURE

The invention is about a procedure for the hydrogenation of olefins in the presence of new catalysts—homogeneous titaniums, that have high activity even without reducing agents. Particularly, this invention refers to hydrogenation catalysts based on mononuclear titanocenes which have a cyclopentadienyl group and a pentamethylcyclopentadienyl group or a ansa-dimethylsilil biscyclopentadienyl or dinuclears that contain a dimethylsilil biscyclopentadienyl bridge and a cyclopentadienyl or pentamethylcyclopentadienyl group. The procedure of the invention can be used for both hydrogenation of olefins of low molecular weight and hydrogenation of double bonds in polymers and copolymers of conjugated dienes in mild reaction conditions.

For the hydrogenation of compounds that contain unsaturated double bonds many catalysts are known which can be classified in two groups:

(1) heterogeneous catalysts, generally consisting of a metal such as Ni, Pd, Pt, Ru, etc., deposited on a carrier such as carbon, silica, alumina, calcium carbonate, etc., and (2) homogeneous catalysts such as: (a) Ziegler catalysts consisting of a combination of an organic salt of Ni, Co, Fe, Cr, etc. and a reducing agent such as organoaluminic compounds or similar and (b) organometallic compounds of Ru, Rh, Ti, La, etc. Heterogeneous catalyst are used widely in industry, but compared to the homogeneous catalysts generally are less active and therefore, to carry out the desired olefin hydrogenation using these heterogeneous catalysts, big quantities of the catalyst are required and the reaction must be carried out at relatively high pressure and temperature. The homogeneous catalysts generally have higher activity; a small amount of the catalyst is enough, and the hydrogenation reaction may be carried out in milder conditions of pressure and temperature. However, homogeneous catalysts have the disadvantage that their stability may not be enough and the isolation of the catalyst or of its decomposition products from the hydrogenated product may be complicated and costly.

The polymers of conjugated dienes such as 1,3-butadiene and isoprene and the copolymers of these dienes with vinylaromatic monomers, for example with styrene, are used widely in industry as elastomers. These polymers contain double bonds in their chain, that allow for their vulcanization but their presence gives a low resistance towards aging and oxidation. Some block copolymers of conjugated dienes and hydrocarbons vinylaromatic are used without vulcanization as thermoplastic elastomers, as impact resistant clear resins, or as polyolefins or polystyrene resin modifiers. However, these copolymers have low resistance to aging and to oxidation due to atmospheric oxygen and ozone, due to the presence of the double bonds in their chain. Then, the use of these copolymers in applications that require exposure to the outside is limited. The resistance to the oxidation by the oxygen and ozone, and in general, the resistance to aging, can be improved by hydrogenating sensibly these polymers to saturate the double bonds totally or partially. Many processes have been proposed for the hydrogenation of polymers containing olefinic double bonds. In general there are two types of processes: processes that use heterogeneous catalysts as mentioned before and processes that use homogeneous Ziegler type catalysts or organometallic compounds of rhodium and titanium.

In the processes that use heterogeneous catalysts, the polymer that is to be hydrogenated is dissolved previously in an appropriate solvent and then is put in contact with hydrogen in the presence of the heterogeneous catalyst. The contact of the reactants with the catalyst is not easy due to the relatively high viscosity of the polymer solution, to steric hindrance of the polymer chain and to the strong adsorption of the polymer, which, once hydrogenated, tends to stay on the surface of the catalyst making it harder for the active centers of the non-hydrogenated polymer to have access. For this, to achieve a complete hydrogenation of the double bonds, great quantities of the catalysts are required and severe reaction conditions, that often cause the decomposition or gelification of the polymer. Also, in the hydrogenation of conjugated dienes copolymers with vinylaromatic hydrocarbons, the aromatic groups are also hydrogenated and is difficult to achieve selective hydrogenation of the double bonds in the polydiene units. In the same way, the physical isolation of the catalysts from the solution of hydrogenated polymer is extremely difficult and sometimes the complete elimination is impossible due to the strong adsorption of the polymer in the heterogeneous catalyst.

In the processes that use Ziegler type catalytic systems, the reaction occurs in a homogeneous media, and therefore, the hydrogenation may be carried out in mild pressure and temperature conditions. Also, by selecting the appropriate hydrogenation conditions, it is possible to hydrogenate selectively the double bonds in the vinylaromatic hydrocarbons and conjugated dienic copolymer chains without hydrogenating the aromatic rings. In effect, the olefinic hydrogenation in the presence of Ziegler-Nata type homogeneous catalysts has been known since the seventies. Only recently the use of this type of catalysts has appeared in enantioselective hydrogenation reactions, R. Wymoth and P. Pinto J. Amer. Chem. Soc. 112, (1991) 4911. However, the elimination of catalytic residues from the reaction products, which is absolutely necessary because these residues affect unfavorably the stability of the hydrogenated polymers, is a complicated and costly step. Other processes that use other homogeneous catalysts, for example the rhodium compounds described in the patent U.S. Pat. No. 3,898,208, have the disadvantage of the high cost of the rhodium catalysts.

The hydrogenation of mono and disubstituted alkenes catalyzed by $Cp_2TiCl(AlH_3)$, a complex prepared from $Cp_2TiCl_2$ and $LiAlH_4$ is also known, H. S. Lee Tashan Hwahakhoe Chi; C.A. 109 (1988) 189899. Titanocenes of the general formula $L_2TiCl_2$ containing L cyclopentadienyl ligands, along with BuLi have been used in the asymmetric hydrogenation of 2-phenyl-1-butene, achieving 34% optical yields, R. L. Halterman and K. P. C. Vllhart, Organometallics 7, (1988) 883.

Zirconium III complexes containing the chelate unit $ZrCH_2PPh_2$, hydrogenate unsaturated hydrocarbons in a fast catalytic process with specific selectivity, yielding quantitatively cyclooctene from 1,3- and 1,5-cyclooctadiene and 1,2,3,4-tetraphenylbutane from diphenylacetilene, R. Chokron, M. Basso-Bert and D. Gervais, J. Chem. Soc. Chem. Commun (1986) 1317.

In the same way, the titanium complex on silica (Sil-$(CH_2)_3C_5H_4)_2TiCl_2$, after the reduction with BuLi is a more efficient and selective catalyst for the hydrogenation of 1-alkenes that the analogous homogeneous catalysts Cp$_2$TiCl$_2$+BuLi, (MeC$_5$H$_4$)$_2$TiCl$_2$+BuLi and ((MeO)$_3$Si-(CH$_2$)$_3$C$_5$H$_4$)TiCl$_2$+BuLi, B. L. Booth et al., J. Organomet. Chem. 315 (1986), 143. Olefins have been hydrogenated with homogeneous catalysts obtained from BuLi and CpTiCl$_2$OC$_6$H$_4$R (R=H, Me, NO$_2$, Cl) or with the products of the reaction of CpTiCl$_3$ with silica-alumina gel, W. Skipinski, Homogeneous Heterog. Catal. Proc. Int. Symp. Relat. Homogeneous Heterog. Catal., 5th (1986) 489, C.A. 107 (1987) 219,436. It is possible to hydrogenate 1-hexene at room temperature and pressure using titanium complexes and active hydrides of alkaline metals, for example, Cp$_2$TiCl$_2$/NaH and (C$_6$H$_{10}$(p-CH$_3$O)C$_5$H$_4$)$_2$TiCl$_2$/NaH.

In the same way, in the patent application G.B. 2159819 A it is indicated that species of the type Cp$_2$TiR$_2$ (R=arylalkyl groups) are catalysts able to hydrogenate selectively the double bonds of conjugated dienic copolymers and polymers.

To achieve more economic hydrogenation processes, industry has the need for more effective homogeneous catalysts than those actually known, that are stable and active in sufficiently low concentrations to be able to avoid the costly step of elimination of catalytic residues from the hydrogenated polymer.

We have discovered that the titanocenes of general formula Cp⊥CpTiR$_2$, Cp∧CpTiR$_2$, Cp∧Cp[CpTiR$_2$]$_2$, Cp∧Cp[Cp⊥TiR$_2$]$_2$, where Cp⊥ is a pentamethylcyclopentadienyl group, Cp is a cyclopentadienyl group and Cp∧Cp are two cyclopentadienyl rings linked by a dimethylsililene (Me$_2$Si) and R is an alkyl, aryl, alkylaryl, o alcoxide group containing between 1 and 20 carbon atoms, or a halogen, a PPh$_2$ group, CH$_2$SiMe$_3$, CH$_2$PPh$_2$ or H are very active homogeneous catalysts in the hydrogenation of linear or branch olefins, internal and external, cyclooolefins, diolefins. These catalysts are also able to hydrogenate selectively the double bonds of the diene groups in conjugated diene copolymers and polymers with vinylaromatic monomers of medium molecular weight in number including between approximately 500 and 1,000,000, and in particular, the random copolymers and block copolymers of styrene/butadiene or isoprene, which contain at least one styrene block and one polybutadiene-1,3 block or polyisoprene.

The high activity of these catalysts makes the catalyst usage per unit weight of hydrogenated polymer very small, which translates as a very low catalysts cost. On the other hand, with the low catalyst concentrations that are generally required, according to this invention, the elimination of the catalyst residues from the hydrogenated polymer is not necessary, since they do not affect unfavorably the properties of the same. As we indicated previously, this is advantageous from the industrial point of view, especially in the hydrogenation of conjugated diene copolymers and polymers since it allows the essential simplification of the process.

Specific examples of usable catalysts in the frame of the invention are:

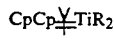

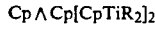

where Cp=η5: C$_5$H$_5$; Cp⊥=η5: C$_5$Me$_5$; Cp Cp=η5: η5 [(Me$_2$Si)(C$_5$H$_4$)$_2$]; and R is an alyl, aryl, alkylaryl, or alcoxide group containing between 1 and 20 carbon atoms or a halogen atom, a —CH$_2$PPh$_2$, —CH$_3$SiMe$_3$, PPh$_2$, or H.

The hydrogenation catalysts according to the invention can be synthesized according to the methods described by R. Gomez, T. Cuenca, P. Royo and E. Hovestreydt, Organometallics 10 (1991) 2516 y B. Demersman, R. Male and P. Dixneuf, J. Chem. Soc. Chem. Commun. (1984) 1394, and as shown in examples 1 to 3 of this document.

The catalysts of this invention can be used to hydrogenate olefins of low molecular weight, those olefins of molecular weight lower than 500, for example, linear olefins such as 1-hexene, branched olefins such as 4-methyl-1-pentene, 4-methyl-2-pentene, etc., cycloolefins such as cyclohexene and cyclooctene, diolefins such as isoprene, 1,3 and 1,5 cyclooctadiene, etc., and are also able to hydrogenate double bonds of vinylic groups of vinylaromatic compounds such as styrene, alpha-methylstyrene, etc.

These catalysts are able to hydrogenate selectively the double bonds of diene groups in conjugated diene copolymers and polymers of medium molecular weight from approximately 500 to 1,000,000 and particularly copolymers of a conjugated diene such as 1,3-butadiene or isoprene and vinylaromatic compounds such as styrene or alpha-methylstyrene. Among these copolymers are included random copolymers in which the comonomers are randomly distributed along the polymer chain, cross-linked copolymers and pure or gradual block copolymers.

The block copolymers are especially interesting since some of them are thermoplastic elastomers usable from the industrial point of view. Such block polymers consist of: a) at least one polymeric block A formed through the polymerization of the aromatic hydrocarbon with one vinylic substituent, such as a styrene or alpha-methylstyrene and b) at least one polymeric block B formed through the polymerization of conjugated dienes such as 1,3-butadiene or isoprene. Among these block copolymers are included linear and branched and radial and star copolymers which are obtained by coupling the linear block copolymers with a coupling agent. The block copolymers used preferably in this invention are the ones that contain between 10 and 90 wt. percent of vinylaromatic hydrocarbon. The preferred copolymers are those which contain approximately 25 to 75 percent of 1,2-vinylic bonds in the conjugated diene groups.

When the block copolymers of these characteristics are hydrogenated the polydiene blocks are transformed into elastic polyolefin blocks in such a way that the copolymers behave as thermoplastic elastomers of great industrial value.

The conjugated diene polymers and the conjugated diene copolymers that can be hydrogenated according to this invention can be obtained by known polymerization methods such as anionic polymerization, cationic polymerization, coordination polymerization, radical polymerization, etc., good for processing in solution, emulsion or plastic form. The anionic polymerization is especially interesting in producing polymers and copolymers that can be hydrogenated according to the invention. Among the initiators that can be used, the organolithium compounds are preferred, particularly butyllithium. The synthesis of diene polymers can be advantageously accomplished with combinations of barium, magnesium, and aluminum compounds, for example alcoxides or barium alkylphosphates, alkylmagnesiums and trialkylaluminiums (Spanish Patent P-9001799). According to a preferred method inside the framework of the invention, the hydrogenation reaction of the unsaturated polymer is accomplish in solution in an inert solvent. In the case of the hydrogenation of low molecular weight compounds which are liquids at room temperature, for example, 1-hexene, cyclohexene or cyclooctene, the hydrogenation can be accomplished without the solvent. The term "inert solvent" means an organic solvent that does not react with any of the reactants that participate in the reaction. Examples of these inert solvents that are recommended inside the frame of this invention are the aliphatic hydrocarbons and cycloaliphatic hydrocarbons such as n-hexane, n-octane, isooctane, cyclohexane, methylcyclopentane, ethers such as tetrahydrofurane, aromatic hydrocarbons such as benzene, toluene, xylene, etc., that are not hydrogenated in the selected reaction conditions, and the mixtures of these compounds.

The reaction may be carried out in tank type reactors with stirring and also in Laso type reactors in which the liquid mixture to be hydrogenated is extracted from the reactor and is circulated by a pump through a heat exchanger and is reintroduced in the reactor where is put into contact with hydrogen. The reaction may be continuous or non-continuous. The catalyst of this invention may be added as is, to the reaction media or in solution dissolved in an inert organic solvent of the type indicated previously.

The amount of catalyst to be used is not critical and may be varied widely. Preferably it should be between 0.001 and 10 millimols per each 100 g of substance to hydrogenate and preferably between 0.01 and 5 mmol. To achieve selective hydrogenation of the double bonds of the conjugated diene copolymers and vinylaromatic compounds, reaction temperatures between 20° and 150° C., preferably between 50° and 100° C., with hydrogen pressures between 1 and 70 kg/cm$^2$, preferably between 4 and 12 kg/cm$^2$, must be used.

The hydrogenation catalysts according to the invention allow to substantially hydrogenate the olefinic double bonds (more than 75%) and due to its high selectivity, they do not appreciably hydrogenate the aromatic groups (less than 1%). In some instances, the partial hydrogenation of the double bonds may be desirable, especially in the case of polymers and copolymers. It can be achieve easily inside the frame of the invention by appropriately choosing the reaction conditions: catalyst type and concentration, temperature, hydrogen pressure, reaction time, etc. Conjugated dienic polymers partially hydrogenated can have interesting applications as compatibility agents in polymer mixtures, as additives to improve rubber processibility and as additives to improve the freezing point of lubricant oils.

The hydrogenation catalysts aim of the invention have in general sufficient activity by themselves and usually do not require the presence of other compounds. However, in some cases it may be advantageous, to increase the activity and/or selectivity of the reaction, reduce them previously or during the reaction, with activated magnesium with mercuric chloride or with reducing organometallic compounds such as organolithiums, organomagnesiums, or organoaluminiums. Examples of the organolithiums indicated are n-butyllithium, butyloctylmagnesium, etc. and of the organoaluminiums, triisobutylaluminium, triethylaluminium, tetrabutylaluminoxane, etc. In the same way, the reaction may be carried out in the presence or absence of Lewis bases such as triphenylphosphine, methyldiphenylphosphine, etc.

The hydrogenation products may be easily isolated from the solvent used through known processes such as distillation, precipitation, etc. In particular partial or totally hydrogenated polymers and copolymers can be separated from the solvent by various procedures:

(1) putting the hydrogenated solution in contact with a polar solvent such as acetone, methanol or similar that cause polymer precipitation and that allow its physical separation.

(2) putting the hydrogenated solution in contact with water in liquid-vapor form and eliminating the solvent by evaporation to obtain a suspension of polymer in water, separating the water and drying the polymer.

(3) evaporating the solvent directly.

As indicated previously, the amount of catalyst that is used inside the frame of the invention can be very small and since the catalyst itself and its decomposition products are not corrosive or give undesirable characteristics to the polymers, usually, the costly polymer purification processes needed to eliminate catalytic residues are not necessary.

The following are some examples that explain the process of the invention which do not assume any limitation of the same:

EXAMPLE 1

Preparation of the catalyst CpCp≠Ti(CH$_2$PPh$_2$)$_2$

In a 250 ml schlenk, with magnetic stirring and under inert atmosphere, 3.83 g of CpCp≠TiCl$_2$ (J. Organomet. Chem. 293 (1985) 51) and 8.13 g of LiCH$_2$PPh$_2$×TMEDA (Inorg. Chem. Vol. 20 (1981) 3206) are introduced. Once the mixture is cooled to $-78°$ C., 100 ml of dry toluene which has been cooled to $-78°$ C. is added. Once the solvent has been added, it is stirred for 30-40 min, while letting it slowly reach room temperature. Under these conditions, stirring is maintained overnight, then the lithium chloride is eliminated by filtration and the solvent by vacuum until dry. A red solid is obtained, that occasionally appeared oily, is washed twice with 40 ml of cold hexane ($-78°$ C.) to eliminate the TMEDA and the traces of free PPh$_2$Me and finally is dried in vacuum. In this way, 7.55 g (97%) of the compound is obtained as a red solid.

EXAMPLE 2

Preparation of the catalyst [Cp ∧ Cp][CpTiCl$_2$]$_2$ a) Obtaining [Cp ∧ Cp]Tl$_2$: 4.6 ml of freshly prepared and free of C$_5$H$_6$ (according to the method described in Inorg. Chem. Vol 24, (1985), 2539; Organometallics (1984), 3, 1470) (Me$_2$Si)(C$_5$H$_5$)$_2$ is introduced in a 200 ml schlenk under inert atmosphere and with magnetic stirring; next 70 ml of dry ether is added and the solution is cooled in an ice-bath. 3.3 ml of TlOEt are added drop by drop and with magnetic stirring, appearing almost instantly is a pale yellow solid in suspension. After two hours of reaction, the solid is decanted, filtered and washed with ether (3×40 ml), eliminating in this way the ethanol formed. Lastly, the solid is dried in vacuum, obtaining 11.46 g (83%).

b) Obtaining [Cp ∧ Cp][CpTiCl$_2$]$_2$: To the thallium salt just prepared (11.46 g), 8.46 g of CpTiCl$_3$ (J. C. S.

Dalton T. (1980), 1156) and 100 ml of dry toluene are added; a bubbling condenser is attached to the schlenk that contains the reaction mixture and with stirring, the mixture is refluxed overnight. As the reaction develops, the change of color from pale yellow to red and the appearance of a white solid in suspension (TlCl) are noted. Following the overnight refluxing, the reaction mixture is cooled to room temperature and the solvent is eliminated until dry. The product is extracted in the soxlet with 100 ml of dichloromethane during 12 h, then is concentrated to a 40 ml volume and cooled between 9° and 30° C. In this way, a microcrystalline red solid is retrieved by filtration, washed with hexane and dried under vacuum (8.30 g 78%).

EXAMPLE 3

Preparation of Cp ∧ Cp[Cp⊥TiMe$_2$]$_2$

Four (4) g of Cp ∧ Cp[TiCp⊥Cl$_2$]$_2$ are introduced into a 250 ml schlenk, prepared following an analogous procedure to the one describe in example 2, and with an inert atmosphere and stirring, 100 ml of dry toluene is added. Then, the reaction mixture is cooled to −78° C. using a dry-ice/acetone bath and 14.4 ml of MeLi (1.6M in ether) are added drop by drop, afterward the bath is taken away and the reaction mixture is let to reach room temperature. As the temperature raises a change in color from red to yellow orange is observed, each time more pale, and the appearance of a white precipitate (LiCl). After 30 min. of stirring at room temperature, the mixture is filtered and the solvent evaporated until dry giving a crystalline yellow product which is slightly oily (3.44 g, 98%). Recrystallization from hexane gives 2.85 g (81%) of the product as a crystalline solid.

EXAMPLE 4

The hydrogenation of olefins of low molecular weight was carried out in a glass autoclave, equipped with an internal pressure and temperature reading system, mechanical stirring, loading system and plugged to a vacuum/inert atmosphere system. Working under constant pressure through a pressure adjusting device placed between the reactor and a tank cylinder at a pressure 2-3 times the working pressure (in that tank any hydrogen consumption is registered) measured by such device.

For identification and analysis of hydrogenation products, the olefin and alkanes, a Perkin-Elmer gas chromatographer with flame ionization detector was used with columns at: a) 15% tricresyl phosphate S/chrom P 60/80, 3m ⅛", with N$_2$ flow 20 ml/min as carrier gas. b) Semicapilar BP1 (no polar) of fused silica 12 m 0.53 mm film: 1 m, with N$_2$ flow 3 ml/min.

To the autoclave, under inert atmosphere, 0.20 mmol of the catalyst CpCp⊥Ti(CH$_2$PPh$_2$)$_2$, prepared according to example 1, is added being dissolved in toluene; 6.7 g of dry, oxygen free 1-hexane as the olefine and it is completed with degassified and dry cyclohexane as solvent to a total volume of 200 ml. Then under vacuum, the reactor gas is evacuated and is heated to 90° C., starting then the stirring and pressurizing the reaction mixture to 7 kg/cm$^2$. After 10 min, the pressure reduction is observed in the tank cylinder, reduction that is maintained for 5 min and then is stabilized. The reaction is assume to be over, the reactor is cooled and depressurized, an aliquot is taken for gas chromatography analysis (GC), observing a 100% conversion.

EXAMPLE 5

Following the same operational hydrogenation procedure described in example 4, in this case the catalyst used was 0.20 mmol of Cp ∧ CpTi(CH$_2$SiMe$_3$)$_2$ dissolved in cyclohexane and 6.7 g of 1-hexene as the olefin, observing a 100% conversion to hexane. Different from last example, hydrogen consumption occurs from the pressurizing moment and it is kept for 60 minutes.

EXAMPLE 6

Following the same operational hydrogenation procedure described in example 4, in this case, 8.1 g of cyclohexene as the olefin and as the catalyst 10 ml of a 0.02M of CpCp⊥TiCl$_2$ in THF are introduced to the reactor. The catalyst was previously reduced in the presence of Mg, in excess (1:20) and activated with HgCl$_2$, overnight. A 100% conversion to cyclohexane is obtained. The activation time in this case was 7.5 min and the hydrogenation time was 30 min.

EXAMPLE 7

Following the same operational hydrogenation procedure described in example 4, but in this case, 16.8 g of a mixture of 65% cis and 35% trans 4-methyl-2-pentene was added to be hydrogenated, introducing as catalyst 10 ml of a solution of 0.02M of CpCp⊥TiCl$_2$ in THF, which was previously reduced with Mg in excess (1:20), activated with HgCl$_2$, in the presence of 1 equivalent of PPh$_2$Me, overnight. Once the reaction is finished a 100% conversion is obtained and it is clearly seen that the cis isomer is hydrogenated without activation time and in 6 min, while the trans isomer starts at 10 min, and it needs 80 min longer to complete hydrogenation, giving the 2-methyl pentane.

EXAMPLE 8

Following the same operational hydrogenation procedure describe in example 4, in this case, as the catalyst, 10 ml of a solution in THF of 0.02M of Cp ∧ CpTiCl$_2$, reduced as described in example 7 and using 16.8 g of a mixture of 4-methyl-2-pentene isomers that is also described in example 7, a 100% conversion to 2-methyl-pentane is obtained. The activation time is zero and no reactivity difference is observed among the olefin isomers. The reaction is completed in 90 min.

EXAMPLE 9

Following the procedure described in example 7 but using as the catalyst 10 ml of a solution in THF of Cp ∧ Cp[Cp⊥TiCl$_2$]$_2$ reduced according to the same example and as olefin 16.8 g of the isomer mixture 4-methyl-2pentene described in example 7, a 65% conversion is observed, reaching 100% of hydrogenation of the cis isomer with activation time of zero and 25 min reaction time; and 0% of the trans isomer after an overnight reaction.

EXAMPLE 10

Using in this case 13.0 g of 1,3-cyclooctadiene as the olefin to be hydrogenated and 0.20 mmol of CpCp⊥Ti(CH$_3$)$_2$ as the catalyst and proceeding as in example 4, a 100% cyclooctane conversion is observed, with an activation time of 85 min and a very short hydrogenation time (5 min).

EXAMPLE 11

Following the procedure described in example 4, but using in this case as olefin 181.8 g of styrene and as catalyst 0.1 mmol of Cp∧Cp[Cp⊻TiMe₂]₂, a 100% ethylbenzene conversion is obtained with 5 min activation and 10 min hydrogenation.

EXAMPLE 12

Polymer hydrogenations were carried out in a 2 L autoclave, with steel beaker, with a temperature control system, variable stirring and hydrogen flow meter, as well as the way of passing the nitrogen and hydrogen, venting and polymer unloading. A SBS (Styrene-Butadiene-Styrene) block copolymer of molecular composition: styrene (27.2%) and butadiene (72.8) (vinylic content of the polybutadiene 10.0%), of MW=164000 and polydispersibility=1.3 was put under hydrogenation.

In the autoclave, 22.5 g of said polymer dissolved in 1450 ml of cyclohexane is loaded, it is degassified and purged several times with nitrogen. It is heated and once 88° C. is reached, 0.85 mmol of CpCp⊥Ti(CH₂PPh₂)₂ is added as a catalyst being dissolved in cyclohexane, which preparation is described in example 1. It is pressurized with hydrogen and a 6 kg/cm² hydrogen pressure is maintained at constant temperature 90° C. throughout the reaction; observing from the moment of pressurization absorption of hydrogen. After 70 min the reaction mixture stops the hydrogen consumption. Assuming the reaction is over, the reactor is cooled, depressurized and the solution obtained is poured over a water vapor-liquid mixture, precipitating a polymer that was then oven dried and its microstructure was analyzed by H-NMR and the molecular weights by GPC (gel permeation chromatography).

The polymer obtained has 93% of the 1,2 polybutadiene groups hydrogenated and 45% of the 1,4 polybutadiene. No hydrogenation of the styrene ring or polymer degradation was observed.

EXAMPLE 13

Following the same procedure as the hydrogenation in example 12, in this case the catalyst used was the titanocene CpCp⊥Ti(CH₃)₂ along with different aluminum compounds. In trials 1 and 2, 22.5 g of the polymer described previously dissolved in 1450 ml of cyclohexane is loaded in the reactor. Once 68° C. is reached, 0.9 mmol of CpCp⊥Ti(CH₃)₂ and 1.8 mmol of the aluminum compound are added, as shown in TABLE 1. It is pressurized with hydrogen and the pressure is kept at 6 kg/cm² and at constant temperature 70° C. throughout the reaction. When the hydrogen consumption ends, the reaction is assumed to be over, the reactor is cooled, depressurized and the solution obtained is poured over a water vapor-liquid mixture, precipitating the polymer. TABLE 1 indicates the hydrogenation times, as well as the hydrogenated polymer conversions obtained.

| Trial | Reducing agent | Time (min) | % 1,2 Hydrog. | % 1,4 Hydrog |
|---|---|---|---|---|
| 1 | TIBA | 80 | 60.1 | 8.8 |
| 2 | TIBAO | 70 | 80.1 | 16.8 |

TIBA = Triisobutylaluminum
TIBAO = Tetraisobutylalumioxane

EXAMPLE 14

Following the same procedure described in example 12, 22.5 g of the same polymer dissolved in 1450 ml of cyclohexane are loaded in the reactor and at 68° C. 0.9 mmol of CpCp⊥Ti(CH₃)₂, 1.8 mmol of n-BuLi and 0.9 mmol of CH₃PPh₂ are added, which were previously mixed. It is pressurized with hydrogen and a hydrogen pressure of 6 kg/cm² and a 70° C. temperature are maintained for 150 min. The isolated polymer contains 100% of the hydrogenated 1,2 polybutadiene groups and 31% of the 1,4. No hydrogenation of the styrene ring or polymer degradation is observed.

EXAMPLE 15

Following the procedure described in example 12, the reactor is loaded with 22.5 g of the copolymer described in such example, dissolved in 1450 ml of cyclohexane, and at a 68° C. temperature, added as catalyst a mixture of 0.9 mmol of CpCp⊥TiCl₂ and 1.8 mmol of n-BuLi dissolved in cyclohexane. A 6 kg/cm² hydrogen pressure and a 70° C. temperature are maintained throughout the 85 min of reaction time. The H-NMR of the isolated polymer microstructure indicates the hydrogenation of 100% for 1,2 polybutadiene and 40% for the 1,4 polybutadiene group.

EXAMPLE 16

The polymer that is hydrogenated in this example is a butadiene-styrene block copolymer prepared from n-BuLi and TMEDA and of molar composition: 41.5% styrene, 58.5% butadiene (vinylic content 49.7% and MW=56000 and polydispersivity index=1.1).

The autoclave is loaded with 22.4 g of the copolymer dissolved in 1450 ml of cyclohexane and following the same procedure describe in example 12, 0.9 mmol of CpCp⊥Ti(CH₂PPh₂)₂ dissolved in cyclohexane is added at 88° C. temperature. It is pressurized with hydrogen and 6 kg/cm² pressure and 90° C. temperature are maintained throughout the reaction. After 230 min the reaction mixture stops the consumption of hydrogen, the reactor is cooled, depressurized and the solution is poured over a water vapor-liquid mixture, precipitating a polymer of which H-NMR indicates that an 80% hydrogenated polybutadiene has been obtained, no styrene ring hydrogenation or polymer degradation was observed.

We claim:

1. A process of olefin hydrogenation in liquid phase, comprising the steps of:
   providing a homogeneous catalyst consisting essentially of:

C₅H₅—C₅(CH₃)₅TiR₂

C₅H₅—(Me₂Si)—C₅H₅TiR₂

C₅H₅—(Me₂Si)—C₅H₅(C₅H₅TiR₂)₂ or

C₅H₅—(Me₂Si)—C₅H₅(C₅(CH₃)₅TiR₂)₂ where R is an alyl, aryl, alkylaryl, or alcoxide group containing between 1 and 20 carbon atoms or a halogen atom, a —CH₂PPh₂, —CH₃SiMe₃, PPh₂, or H; and
   contacting the catalyst with an olefin in liquid phase under effective hydrogenation conditions, whereby the olefin is hydrogenated.

2. The process of claim 1, comprising reducing the described catalysts with activated magnesium, with mercuric chloride, or with reducing organometallic compounds before and during the hydrogenation.

3. The process of claim 1, comprising carrying out the reaction in the presence of a Lewis base.

4. The process of claim 1, wherein the olefins are linear, branched olefins, cycloolefins and diolefins of molecular weight less than 500, and the reaction is carried out in the presence of an inert solvent.

5. The process of claim 1, wherein the olefin is a dienic polymer or a dienic copolymer with vinylaromatic hydrocarbons, of molecular weight between approximately 500 and 1,000,000, in solution in an inert solvent.

6. The process of claim 1, wherein the hydrogenation is carried out at temperatures between approximately 20° and 150° C., preferably between 50° and 100° C., with hydrogen pressures between approximately 1 and 70 kg/cm$^2$, preferably between 4 and 12 kg/cm$^2$.

7. The process of claim 1, wherein the catalyst amounts to between approximately 0.001 and 10 millimols for each 100 grams of substance to be hydrogenated and more preferably between 0.01 and 5 millimols.

8. The process of claim 4, 5, 6 or 7 wherein the copolymer consists mainly of a) 1,3butadiene and/or isoprene and b) styrene.

9. The process of claim 8 wherein the copolymer is a block copolymer containing at least one polymeric block A consisting of styrene and at least one polymeric block B consisting mainly of 1,3-butadiene and/or isoprene, being the content of block A in the copolymer of 10–90 wt. percent and the content in the 1,2-vinylic groups in block B of 25 to 75%.

10. The process of claim 8 wherein more than 75% of the 1,3-butadiene and/or isoprene groups and less than 1% of the styrene groups are hydrogenated.

* * * * *